(12) United States Patent
Waksal et al.

(10) Patent No.: US 9,586,940 B2
(45) Date of Patent: Mar. 7, 2017

(54) METHODS FOR TREATMENT OF BREAST CANCER NONRESPONSIVE TO TRASTUZUMAB

(71) Applicant: KADMON CORPORATION, LLC, New York, NY (US)

(72) Inventors: Samuel Waksal, New York, NY (US); Lillian Chiang, Princeton, NJ (US)

(73) Assignee: KADMON CORORATION, LLC, New York, NY (US)

( * ) Notice: Subject to any disclaimer, the term of this patent is extended or adjusted under 35 U.S.C. 154(b) by 0 days.

(21) Appl. No.: 14/801,335

(22) Filed: Jul. 16, 2015

(65) Prior Publication Data

US 2015/0322046 A1    Nov. 12, 2015

Related U.S. Application Data

(63) Continuation of application No. 14/369,348, filed as application No. PCT/US2012/071883 on Dec. 27, 2012, now abandoned.

(60) Provisional application No. 61/580,543, filed on Dec. 27, 2011.

(51) Int. Cl.
| | |
|---|---|
| *A61K 31/517* | (2006.01) |
| *C07D 239/94* | (2006.01) |
| *C07D 403/12* | (2006.01) |
| *A61K 39/395* | (2006.01) |
| *C07K 16/32* | (2006.01) |
| *A61K 39/00* | (2006.01) |

(52) U.S. Cl.
CPC ........... *C07D 403/12* (2013.01); *A61K 31/517* (2013.01); *A61K 39/3955* (2013.01); *A61K 39/39558* (2013.01); *C07K 16/32* (2013.01); *A61K 2039/505* (2013.01); *A61K 2039/55511* (2013.01)

(58) Field of Classification Search
CPC ............................. C07D 239/94; A61K 31/517
USPC ........................................ 544/326; 514/258.1
See application file for complete search history.

(56) References Cited

U.S. PATENT DOCUMENTS

| | | |
|---|---|---|
| 7,576,074 B2 | 8/2009 | Rice et al. |
| 2009/0017024 A1 | 1/2009 | Estok et al. |
| 2009/0318373 A1 | 12/2009 | Rice et al. |
| 2010/0209420 A1 | 8/2010 | Lamb et al. |
| 2011/0123434 A1 | 5/2011 | Lamb et al. |

FOREIGN PATENT DOCUMENTS

| | | |
|---|---|---|
| EP | 2 330 131 A2 | 6/2011 |
| JP | 2011-121943 A | 6/2011 |

OTHER PUBLICATIONS

Gendreau et al, Cancer Therapy: Preclinical, 2007, pp. 3713-3723.*

(Continued)

*Primary Examiner* — Kamal Saeed
*Assistant Examiner* — Janet L. Coppins
(74) *Attorney, Agent, or Firm* — Fox Rothschild LLP

(57) ABSTRACT

The present invention provides a method of treating breast cancer that is nonresponsive to treatment with trastuzumab, comprising administering to a subject in need of such treatment a therapeutically effective amount of compound N-(3,4-dichloro-2-fluorophenyl)-7-({[(3aR,6aS)-2-methyl-octahydrocyclopenta[c]pyrrol-5-yl]methyl}oxy)-6-(methyl-oxy)quinazolin-4-amine, or a pharmaceutically acceptable salt thereof.

10 Claims, 10 Drawing Sheets

(56) References Cited

OTHER PUBLICATIONS

Bose, Prithviraj et al., "Neratinib: an oral, irreversible dual EGFR-HER2 inhibitor for breast and non-small cell lung cancer," Expert Opinion on Investigational Drugs, vol. 18, No. 11, Nov. 1, 2009, pp. 1735-1751.

Solca, Flavio F. et al., "Beyond Trastuzumab: Second-Generation Targeted Therapies for HER-2-positive Breast Cancer," Dec. 9, 2010, M. Sibilia et al. (eds.) Drugs for HER-2-positive breast cancer, Milestones in Drug Therapy, pp. 91-107.

Tsang et al,, "Lapatinib, a Dual-Targeted Small Molecule Inhibitor of Egfr and Her2, in Her2-Amplified Breast Cancer: From Bench to Bedside," Clinical Medicine Insights: Therapeutics, Jan. 1, 2011, (p. 1) pp. 1-13.

* cited by examiner

BT474 xenografts in mice

Dose Response:
(QD x 3)

Kinetics:
(single dose)

A.

B.

C.

D.

METHODS FOR TREATMENT OF BREAST CANCER NONRESPONSIVE TO TRASTUZUMAB

CROSS-REFERENCE TO RELATED APPLICATIONS

This application claims priority to U.S. Application No. 61/580,543, filed Dec. 27, 2011, which is incorporated herein by reference in its entirety.

FIELD OF THE INVENTION

The present invention concerns methods for treating breast cancer by administering the compound N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine, or a pharmaceutically acceptable salt thereof, to a subject in need of such treatment. The present invention particularly concerns methods where the breast cancer is nonresponsive to treatment with trastuzumab.

BACKGROUND

Breast cancer is a type of cancer that forms in tissues of the breast, usually the ducts and lobules. It occurs in both men and women, although male breast cancer is rare. It is estimated that in the United States approximately 230,000 new cases of breast cancer will arise in the year 2011, and about 40,000 deaths will occur that result from this form of cancer. See the website of the National Cancer Institute (NCI) at www.cancer.gov.

The ErbB2 (Her2/Neu) oncogene is overexpressed in 20-30% of human breast cancers and this overexpression is associated with poor prognosis and poor response to chemotherapy. ErbB2 is a 185-kDa type I tyrosine kinase transmembrane receptor that is a member of the epidermal growth factor receptor (EGFR) family. This family includes EGFR, ErbB2, Her3 and Her4. There is no known ligand for ErbB2, but this receptor has been shown to be the preferential heterodimerization partner for other ErbB family members that bind growth factors in the EGF, transforming growth factor-β, and heregulin families. The ErbB2 pathway promotes cell growth and division when it is functioning normally. While the precise mechanism of ErbB2 pathway activation in ErbB2-overexpressing cells is not entirely understood, overexpression likely leads to increased cell growth. See Chan et al., 2005, Breast Cancer Res. Treat., 91:187-201.

Trastuzumab (marketed under the name Herceptin® by Genentech) is a recombinant humanized monoclonal antibody that binds to the extracellular segment of the ErbB2 receptor. Trastuzumab is used as a single agent or in combination with chemotherapy and other targeted therapies to treat patients with breast cancer overexpressing ErbB2. Trastuzumab shows considerable clinical efficacy and has been shown to extend the overall survival of certain patients with ErbB2-overexpressing breast cancer. See Chan et al., 2005, Breast Cancer Res. Treat., 91:187-201.

Despite trastuzumab's general clinical efficacy of about 50% responsiveness, many patients do not respond to trastuzumab treatment at all (de novo nonresponsiveness), or acquire nonresponsiveness to trastuzumab treatment during the course of treatment. Postulated mechanisms of trastuzumab nonresponsiveness include: activation of the phosphoinositide 3-kinase (PI3K) pathway due to, for example, mutations in the PIK3CA gene; lack or inactivity of the tumor suppressor PTEN (phosphatase and tensin homolog); accumulation of truncated ErbB2 receptors (p95HER2) that cannot be inactivated by trastuzumab because they lack the extracellular domain to which trastuzumab usually binds; and overexpression of other RTKs that compensates for trastuzumab-induced ErbB2 inhibition. Examples of such RTKs include members of the epidermal growth factor receptor (EGFR) family, the insulin-like growth factor-1 receptor (IGF-1R) and the hepatocyte growth factor receptor (HGFR). See Zhang et al., 2011, Nat. Med., 17(4):461-468; see also Chan et al., 2005, Breast Cancer Res. Treat., 91:187-201.

Recently, it was demonstrated that the SRC kinase is a common node downstream of multiple pathways that result in tumors that are de novo nonresponsive or that have acquired nonresponsiveness to trastuzumab. See Zhang et al., 2011, Nat. Med., 17(4):461-468. The non-receptor tyrosine kinase SRC is a cytoplasmic protein that consists of three domains, an N-terminal SH3 domain, a central SH2 domain and a tyrosine kinase domain. SRC facilitates intracellular signal transduction by interacting with multiple RTKs through its SH2 domain and by phosphorylating and thus activating downstream targets. Examples of pathways and proteins activated by the SRC kinase include the AKT and the MAPK (mitogen-activated protein kinases) pathways, FAK (focal adhesion kinase), STAT3 (signal transducer and activator of transcription-3) and c-MYC. These signaling pathways and proteins have diverse roles in regulating tumor cell survival and metastasis. See Zhang et al., 2011, Nat. Med., 17(4):461-468.

It was found that SRC is activated (i.e., phosphorylated) in a model of acquired trastuzumab nonresponsiveness, wherein cultured cells overexpress EGFR or IGF-1R. Moreover, SRC is activated in PTEN-deficient cells in a model of de novo trastuzumab nonresponsiveness and in vitro GST pull-down assays demonstrated that SRC is a direct target of PTEN's phosphatase activity. On the other hand, SRC is inactivated (i.e., dephosphorylated) when, for example, the expression of EGFR is reduced, or when originally PTEN-deficient cells are reconstituted with wildtype PTEN. Furthermore, it was found that certain cells stably expressing a constitutively active SRC mutant are highly resistant to trastuzumab-mediated growth inhibition in vitro and in vivo, suggesting that SRC activation is sufficient to confer trastuzumab nonresponsiveness. The same study showed that SRC activity in human cancer specimens positively correlates with a lower clinical rate of response to trastuzumab treatment and that inhibition of SRC by saracatinib increases responsiveness of tumors to trastuzumab. See Zhang et al., 2011, Nat. Med., 17(4):461-468.

SUMMARY OF THE INVENTION

The present invention provides a method of treating breast cancer that is nonresponsive to treatment with an extracellular HER2 antagonist, comprising administering to a subject in need of such treatment a therapeutically effective amount of a compound of Formula 1

Formula 1

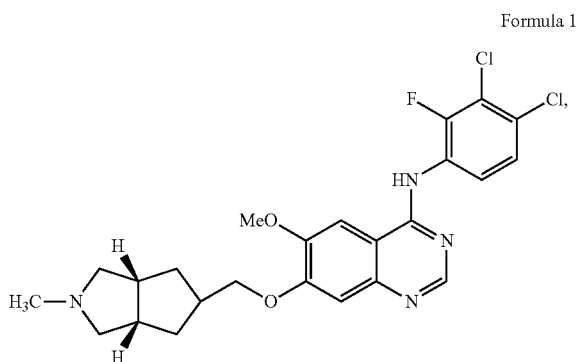 [SMILES: COc1cc2c(Nc3ccc(Cl)c(Cl)c3F)ncnc2cc1OCC1C[C@@H]2CN(C)C[C@@H]2C1]

or a pharmaceutically acceptable salt thereof.

The present invention further provides a compound of Formula 1, or a pharmaceutically acceptable salt thereof, for use in treating breast cancer that is nonresponsive to treatment with trastuzumab.

The present invention further provides the use of a compound of Formula 1, or a pharmaceutically acceptable salt thereof, for the manufacture of a medicament for treating breast cancer that is nonresponsive to treatment with trastuzumab.

The present invention also provides a method of treating HER2-positive cancer that is nonresponsive to treatment with an extracellular HER2 antagonist, comprising administering to a subject in need of such treatment a therapeutically effective amount of a compound of Formula 1, or a pharmaceutically acceptable salt thereof.

The present invention also provides a method of treating EGFR-dependent cancer that is nonresponsive to treatment with an extracellular EGFR antagonist, comprising administering to a subject in need of such treatment a therapeutically effective amount of a compound of Formula 1, or a pharmaceutically acceptable salt thereof.

In certain embodiments of the present invention, the compound of Formula 1 is N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine or N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine. In another embodiment of the present invention, the pharmaceutically acceptable salt is the salt of p-toluenesulfonic acid.

In some embodiments of the present invention, the subject is human and the breast cancer has not previously been treated with trastuzumab. In other embodiments of the present invention, the subject is human and the breast cancer has been previously treated with trastuzumab. In other embodiments of the present invention, the method comprises co-administering a compound of Formula 1 and trastuzumab.

In some embodiments of the present invention, the subject is human and the breast cancer is PTEN-negative. In other embodiments of the present invention, the subject is human and the breast cancer is positive for mutations in the PIK3CA gene. In other embodiments, the subject is human and the breast cancer expresses a truncated ErbB2 receptor that lacks the extracellular domain to which trastuzumab usually binds. In other embodiments of the present invention, the subject is human and the breast cancer overexpresses RTKs, for example members of the EGFR family, IGF-1R and HGFR.

DETAILED DESCRIPTION OF THE INVENTION

Figure 1:
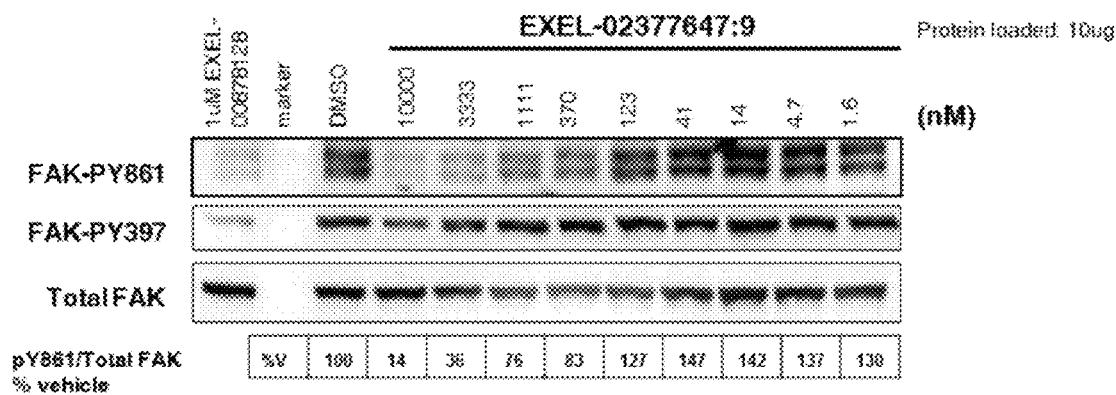
FIG. 1 shows the effect of EXEL-7647 on SRC kinase activity and on the phosphorylation of the SRC family protein FAK (focal adhesion kinase).

The present invention provides a method of treating HER2 positive cancer, including breast cancer, that is nonresponsive to treatment with an extracellular HER2 antagonist, comprising administering to a subject in need of such treatment a therapeutically effective amount of a compound of Formula 1

Formula 1

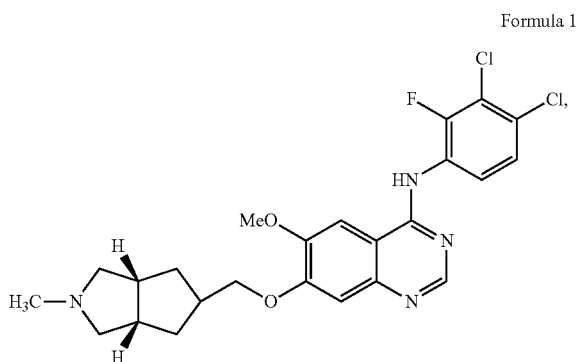 [SMILES: COc1cc2c(Nc3ccc(Cl)c(Cl)c3F)ncnc2cc1OCC1C[C@@H]2CN(C)C[C@@H]2C1]

or a pharmaceutically acceptable salt thereof. The chemical name of the compound of Formula 1 is N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine.

The compound of Formula 1, and its pharmaceutically acceptable salts, includes stereoisomers, enantiomers, diastereomers, racemates, and racemic or non-racemic mixtures thereof, as well as any pharmaceutically acceptable salts of said stereoisomers, enantiomers, diastereomers, racemates and racemic or non-racemic mixtures.

In an embodiment of the invention, the compound of Formula 1 is N-(3,4-dichloro-2-fluorophenyl)-7-({[(3 aR,5r,6aS)-2-methyloctahydrocyclopenta[c]pyrrol-5-yl]methyl}oxy)-6-(methyloxy)quinazolin-4-amine or N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, or a pharmaceutically acceptable salt thereof. In another embodiment of the invention, the pharmaceutically acceptable salt is the salt of p-toluenesulfonic acid.

As used herein, the term pharmaceutically acceptable salt(s) includes pharmaceutically acceptable acid addition salts. Pharmaceutically acceptable acid addition salts are salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, hexanoic acid, heptanoic acid, cyclopentanepropionic acid, glycolic acid, pyruvic acid, lactic acid, malic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, stearic acid, and the like. A preferred pharmaceutically acceptable acid addition salt is the salt of p-toluenesulfonic acid.

The compound of Formula 1 and pharmaceutically acceptable salts thereof can be manufactured using techniques commonly known in the art. For example, said compound and pharmaceutically acceptable salts thereof, as well as methods of manufacturing them, are disclosed in U.S. Pat. No. 7,576,074, which is incorporated herein by reference. U.S. Pat. No. 7,576,074 was assigned from Exelixis, Inc. to Symphony Evolution, Inc. on Jun. 10, 2009. Kadmon Corporation, LLC has acquired certain rights to the compound of Formula 1 (also known as XL647, EXEL-7647 and KD-019), including data provided in the Examples below.

Gendreau et al. describes certain research studies conducted by Exelixis, Inc. concerning the pharmacological properties of XL647. Specifically, this study showed that XL647 is an in vitro inhibitor of several receptor tyrosine kinases (RTKs), including EGFR, EphB4, KDR (VEGFR), Flt4 (VEGFR3) and ErbB2. Furthermore, in vivo experiments showed that XL647 inhibits the activity of EGFR in xenograft tumors derived from A431 epidermal carcinoma cells, and that it inhibits the growth of xenograft tumors derived from MDA-MB-231 human breast cancer cells, which overexpress VEGFR. See Gendreau et al., 2007, Clin. Cancer Res., 13:3713-3723.

The Examples set forth below demonstrate that the compound of Formula 1, in addition to being an inhibitor of several receptor tyrosine kinases (RTKs), is also an inhibitor of the SRC kinase, which is involved in multiple pathways that result in nonresponsiveness of ErbB2-overexpressing tumors to trastuzumab. Accordingly, the present invention now provides a method of treating breast cancer, e.g., breast cancer, that is nonresponsive to treatment with an extracellular HER2 antagonist, including but not limited to trastuzumab, comprising administering to a subject in need of such treatment a therapeutically effective amount of a compound of Formula 1, or a pharmaceutically acceptable salt thereof.

An extracellular HER2 antagonist is an agent that binds to the extracellular portion of HER2 and reduces or inhibits its function. In one embodiment, the HER2 antagonist is an antibody or antigen binding fragment, or conjugate thereof, that binds to the extracellular portion of HER2. In an embodiment of the invention, the HER2 antagonist is trastuzumab. While treatment with trastuzumab has been observed to increase HER2 phosphorylation, trastuzumab treatment also leads to internalization and degradation of HER2 and a reduction in HER2 signaling. Thus, trastuzumab may be considered a HER2 antagonist according to the invention. In another embodiment of the invention, the HER2 antagonist is trastuzumab emtansine (trastuzumab-DM1; T-DM1). In another embodiment, the HER2 antagonist is pertuzumab.

Amplification or over-expression of HER2 has been shown to play an important role in the pathogenesis and progression not only of certain types of breast cancer, but other types of cancer as well. Accordingly, the methods disclosed herein are useful to treat HER2-positive cancers including, without limitation, breast cancer, ovarian cancer, such as ovarian epithelial cancer, ovarian germ cell tumor, non-small cell lung cancer, stomach cancer, esophageal cancer, gastric cancer, uterine cancer, endometrial cancer, prostate cancer, bladder cancer, glioblastoma, metastatic solid tumors characterized by Her2 expression, or any other cancer that expresses HER2. The cancers to be treated include early and late stage cancers.

The invention also provides a method of treating cancer that is nonresponsive to treatment with an extracellular EGFR antagonist, comprising administering to a subject in need of such treatment a therapeutically effective amount of a compound of Formula 1. In an embodiment of the invention, the EGFR antagonist is an antibody or antigen binding fragment, or conjugate thereof, that binds to the extracellular portion of EGFR. In one embodiment, the EGFR antagonist is cetuximab. In another embodiment, the EGFR antagonist is mAB806, which binds to EGFR as well as the truncated EGFRvIII mutant. In another embodiment, the EGFR antagonist is panitumumab. In another embodiment, the EGFR antagonist is zalutumumab. In yet another embodiment, the EGFR antagonist is nimotuzumab. In another embodiment, the EGFR antagonist is matuzumab. Cancers in which EGFR plays a role include, without limitation, colorectal cancer, head and neck cancers, and non-small cell lung cancers.

Nonresponsive, ErbB2-overexpressing cancer is either de novo nonresponsive or has acquired nonresponsiveness to treatment with trastuzumab. De novo nonresponsive either means that the ErbB2-overexpressing breast cancer, in the course of treatment with trastuzumab, does not go into partial or complete remission, or, alternatively, that this cancer is characterized by one or more molecular deficiencies which make it incapable of going into partial or complete remission in response to trastuzumab treatment. Non-limiting examples of such molecular deficiencies may include the activation of the phosphoinositide 3-kinase (PI3K) pathway due to, for example, mutations in the PIK3CA gene; the lack or inactivity of the tumor suppressor PTEN; the accumulation of truncated ErbB2 receptors; increased heregulin-mediated autocrine signaling; and the overexpression of other RTKs, such as members of the epidermal growth factor receptor (EGFR) family, the insulin-like growth factor-1 receptor (IGF-1R) and the hepatocyte growth factor receptor (HGFR). As provided further below, all of these molecular deficiencies can be detected by standard molecular biological techniques commonly known in the art. Acquired nonresponsiveness, as used herein, means that the ErbB2-overexpressing breast cancer, in the course of treatment with trastuzumab, initially goes into remission, but then recurs. A cancer, such as a breast cancer, that has acquired reduced responsiveness to trastuzumab or has acquired nonresponsiveness to trastuzumab may also be referred to as trastuzumab resistant.

EGFR-dependent cancers also acquire reduced responsiveness or become nonresponsive to cetuximab or other therapeutic EGFR antibodies by several mechanisms, including those set forth above for HER2. For example, EGFR-dependent cancers may become nonresponsive when bypassed by a HER2 signaling mechanism. De novo or acquired nonresponsiveness may also result from mutations in KRAS, BRAF, and NRAS.

Remission is a decrease in or disappearance of signs and symptoms of cancer. In partial remission, some, but not all, signs and symptoms of cancer have disappeared. In complete remission, all signs and symptoms of cancer have disappeared, although cancer still may be in the body. In order to determine whether breast is in remission, the subject is generally evaluated using the same techniques that are commonly used for initial breast cancer detection and diagnosis, such as, for example, mammography, ultrasound, ductography, positron emission mammography (PEM) and magnetic resonance imaging (MRI). The thus obtained data, are then compared with the corresponding data obtained when the breast cancer was originally diagnosed and it is concluded, based on standard oncological practice, whether the signs and symptoms of breast cancer have partially or completely disappeared, i.e., whether the breast cancer is in partial or complete remission. The person of skill in the art may find that the breast cancer is in partial remission, for example, because the size of the breast cancer is reduced by comparison to the size of the breast cancer at the time the breast cancer was originally diagnosed. Alternatively, the person of skill in the art may find that the breast cancer is in partial remission because the cancer has stabilized or because the growth of the cancer is reduced. The breast cancer may be considered to be in remission because the signs and symptoms of the breast cancer are reduced by, for example, 10, 20, 30, 40, 50, 60, 70, 80, 90 or 100%.

In some embodiments of the present invention, the subject is human and the breast cancer has been previously treated with trastuzumab. In other embodiments of the present invention, the subject is human and the breast cancer has not previously been treated with trastuzumab. As set forth above, whether or not breast cancer will be nonresponsive to trastuzumab treatment can be determined based on the presence or absence in the breast cancer of certain molecular deficiencies.

In one embodiment of the present invention, the compound of Formula 1, or a pharmaceutically acceptable salt thereof, is co-administered with a HER2 antagonist. Provided its Src inhibitory activity, the compound of Formula 1 can increase the effectiveness of the HER2 antagonist. Alternatively or in addition, co-administration of a compound of Formula 1 with a HER2 antagonist can delay or prevent the onset of resistance to either agent. HER2 antagonists include, without limitation, extracellular antagonists, such as anti-HER2 antibodies (e.g., trastuzumab, pertuzumab) and conjugates thereof, and intracellular antagonists (e.g., lapatinib, canertinib, neratinib, afatinib). The compound of Formula 1, or a pharmaceutically acceptable salt thereof, and the second agent can be administered in a single formulation or as separate formulations. In certain embodiments, for example, the compound of Formula 1, or a pharmaceutically acceptable salt thereof, may be administered orally and trastuzumab intravenously. Other routes of administration are also possible. The compound of Formula 1, or a pharmaceutically acceptable salt thereof, can be co-administered with trastuzumab in such a way that it is administered before or after trastuzumab, or at the same time.

The compound of the present invention, or a pharmaceutically acceptable salt thereof, can also be co-administered with a variety of other drugs in the manner described above for the co-administration with a HER2 antagonist. The term drugs as used herein refers to any compound with therapeutically beneficial properties. In certain embodiments of the invention, the treatment method further comprises administering to the subject trastuzumab, or other antibody therapeutic effective against or being developed to treat cancer such as cetuximab or nimotuzumab (anti-EGFR antibodies), cixutumumab (IMC-A12), ganitumab (AMG-479), dalotuzumab (MK-0646), MEDI-573, RG-1507, and AVE-1642 (anti-IGF-1R antibodies in clinical development). In certain embodiments of the invention, the method further comprises administering to the subject a small molecule tyrosine kinase inhibitor, including but not limited to erlotinib, gifitinib (EGFR inhibitors), AP26113 (dual EGFR, ALK inhibitor), NVP-AEW541, CP-751,871, and BMS-536924 (IGF-1R inhibitors).

In certain embodiments of the invention, the treatment method further comprises administering to the subject an antagonist of hepatocyte growth factor (HGF) or MET tyrosine kinase disclosed in Comoglio et al., (*Nature Reviews Drug Discovery*, June 2008, vol. 7, pp. 504-516, hereby incorporated by reference), including NK2 (a fragment of HGF containing the amino terminal hairpin and the first two Kringle domains), NK4 (a HGF fragment containing the α-chain and not the β-chain), uncleavable HGF, decoy MET, the isolated Sema domain of MET, various fully human monoclonal antibodies to HGF disclosed in Burgess et al. (*Cancer Res.*, 66:1721-1729, 2006), ficlatuzumab, TAK-701 (L2G7), onartuzumab, ALD-805, ALD-806, rilotumumab (AMG102) (anti-HGF monoclonal antibodies), antibodies against MET such as LY-2875358, HuMax-cMet, LA-480, OA-5D5 and DN30, and small molecule MET inhibitors such as K252, SU11274, PHA665752, crizotinib (PF2341066), foretinib (XL880), ARQ197, MK2461, MP470, SGX523, and JNJ38877605. Additional agents that may be coadministered according to the invention include, cabozantinib (XL184), MGCD-265, SAR-125844, E-7050, INCB-028060, EMD-94283, EMD-1214063, EMD-1204831, LY-2801653, LY-2875358, MK8033, and AMG-208.

In certain embodiments of the invention, the treatment method further comprises administering to the subject an agent that modulates the PI3K/Akt or MEK pathways, including but not limited to, dasatinib, bosutinib, saracatinib, everolimus, temsirolimus, ridaforolimus, vemurafenib, and sorafenib.

In the methods of the invention, the compound of Formula 1 can be administered by routes commonly known in the art. This includes oral administration, or any other convenient route. The compound of Formula 1 may also be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, transmucosal, rectally, by inhalation, or topically, particularly to the ears, nose, eyes, or skin. The mode of administration is left to the discretion of the practitioner. In most instances, administration will result in the release of a compound into the bloodstream.

In specific embodiments, it may be desirable to administer a compound locally. This may be achieved, for example, and not by way of limitation, by local infusion, topical application, by injection, by means of a catheter, by means of a suppository, or by means of an implant, said implant being of a porous, non-porous, or gelatinous material, including membranes, such as sialastic membranes, or fibers. In such instances, administration may selectively target a local tissue without substantial release of a compound into the bloodstream.

Pulmonary administration can also be employed, e.g., by use of an inhaler or nebulizer, and formulation with an aerosolizing agent, or via perfusion in a fluorocarbon or synthetic pulmonary surfactant. In certain embodiments, a compound is formulated as a suppository, with traditional binders and vehicles such as triglycerides.

In another embodiment, a compound is delivered in a vesicle, in particular a liposome (See Langer, 1990, Science 249:1527-1533; Treat et al., in Liposomes in the Therapy of Infectious Disease and Bacterial infection, Lopez-Berestein and Fidler (eds.), Liss, New York, pp. 353-365 (1989); Lopez Berestein, ibid., pp. 317-327; see generally ibid.).

In another embodiment, a compound is delivered in a controlled release system (See, e.g., Goodson, in Medical Applications of Controlled Release, supra, vol. 2, pp. 115-138 (1984)). Examples of controlled-release systems are discussed in the review by Langer, 1990, Science 249:1527-1533 may be used. In one embodiment, a pump may be used (See Langer, supra; Sefton, 1987, CRC Crit. Ref Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105).

The present invention provides a method of treating breast cancer in a subject. The term subject, as used herein, refers to the animal being treated, wherein the animal can be a mammal such as a human.

The therapeutically effective amount of the compound of Formula 1 is the dose of this compound, or of a pharmaceutically acceptable salt thereof, that provides a therapeutic benefit in the treatment or management of cancer, delays or minimizes one or more symptoms associated with cancer, or enhances the therapeutic efficacy of another therapeutic agent used in the treatment or management of cancer. The therapeutically effective amount may be an amount that reduces or inhibits the growth of breast cancer. A person skilled in the art would recognize that the therapeutically effective amount may vary depending on known factors such as the pharmacodynamic characteristics of the particular active ingredient and its mode and route of administration; age, sex, health and weight of the recipient; nature and extent of symptoms; kind of concurrent treatment, frequency of treatment and the effect desired. A person skilled in the art would also recognize that the therapeutically effective amount, or dose, of the compound of Formula 1 can be determined based on the disclosures in this patent application and common knowledge in the art.

The amount of a compound, or the amount of a composition comprising a compound, that will be effective in the treatment and/or management of cancer can be determined by standard clinical techniques. In vitro or in vivo assays may optionally be employed to help identify optimal dosage ranges.

In some cases, the dosage of a compound may be determined by extrapolating from the no-observed-adverse-effective-level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005. In one embodiment, a compound or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

A dosage regime for a human subject can be extrapolated from animal model studies using the dose at which 10% of the animals die ($LD_{10}$). In general the starting dose of a Phase I clinical trial is based on preclinical testing. A standard measure of toxicity of a drug in preclinical testing is the percentage of animals that die because of treatment. It is well within the skill of the art to correlate the $LD_{10}$ in an animal study to a maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or cancer to target are also factors to consider. In one embodiment, the standard conservative starting dose is about 1/10 the murine $LD_{10}$, although it may be even lower if other species (i.e., dogs) were more sensitive to the compound. In other embodiments, the standard conservative starting dose is about 1/100, 1/95, 1/90, 1/85, 1/80, 1/75, 1/70, 1/65, 1/60, 1/55, 1/50, 1/45, 1/40, 1/35, 1/30, 1/25, 1/20, 1/15, 2/10, 3/10, 4/10, or 5/10 of the murine $LD_{10}$. In other embodiments, an starting dose amount of a compound in a human is lower than the dose extrapolated from animal model studies. In another embodiment, a starting dose amount of a compound in a human is higher than the dose extrapolated from animal model studies. It is well within the skill of the art to start doses of the active composition at relatively low levels, and increase or decrease the dosage as necessary to achieve the desired effect with minimal toxicity.

In some of the embodiments of the present invention, the compound of Formula 1, or a pharmaceutically acceptable salt thereof, may be used at a dose of between about 0.01 mg/kg of patient body weight per day and about 10 mg/kg of patient body weight per day, and preferably between about 0.05 mg/kg of patient body weight per day and about 5 mg/kg of patient body weight per day. Accordingly, daily doses include, without limitation, 1000 mg/day, 750 mg/day, 500 mg/day, 300 mg/day, 250 mg/day, 100 mg/day, and 50 mg/day.

The compound of the present invention, and its pharmaceutically acceptable salts, may be formulated in a pharmaceutical composition. In certain embodiments provided herein, the composition may comprise said compound and a pharmaceutically acceptable carrier, excipient, or diluent. The pharmaceutical compositions provided herein can be in any form that allows for the composition to be administered to a subject, including, but not limited to a human, and formulated to be compatible with an intended route of administration.

The ingredients of compositions provided herein may be supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutically acceptable carriers, excipients and diluents include those approved by a regulatory agency of the Federal or a state government or listed in the U.S. Pharmacopeia or other generally recognized pharmacopeia for use in animals, and more particularly in humans. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Preferred lactose free dosage forms comprise a compound, microcrystalline cellulose, pre gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a therapeutically effective amount of a compound preferably in purified form, together with a suitable amount of carrier so as to provide the form for proper administration to the patient.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

In some embodiments of the present invention, the breast cancer is PTEN-negative. The term PTEN-negative refers to breast cancer in which at least some cancer cells lack any detectable amount of human PTEN protein or contain a significantly reduced amount, or in which at least some cancer cells lack a human PTEN gene, carry a null-mutation in the human PTEN gene or carry a mutation that significantly reduces the expression and/or function of the human PTEN protein. The PTEN tumor suppressor gene has been extensively researched. See. e.g., Li et al., 1997, Science 275:1943-1947; Steck et al., 1997, Nat Genet. 15: 356-362. Molecular biological, immunohistochemical and other methods for detecting human PTEN protein, or the absence thereof, in tumor tissue and for detecting mutations in the human PTEN gene are commonly known in the art and disclosed, for example, in U.S. Pat. No. 7,981,616, the disclosure of which is incorporated herein by reference. For instance, a breast cancer biopsy sample can be obtained and analyzed immunohistochemically for human PTEN expression by using a PTEN-specific antibody and appropriate secondary detection reagents. PTEN-specific antibodies are available commercially from many sources, including, Abcam and Cell Signaling Technology. Human PTEN protein expression thus determined can be classified as absent or reduced by comparison to, for example, the expression of internal molecular markers, e.g., actin and other ubiquitously expressed proteins, by comparison to PTEN expression in normal tissue surrounding the tumor, or as set forth in U.S. Pat. No. 7,981,61. Mutations of the human PTEN gene can be detected, for example, as described below for the analysis of the human PIK3CA gene.

In other embodiments of the present invention, the breast cancer is positive for mutations in the human PIK3CA gene. A breast cancer that is positive for mutations in the PIK3CA gene includes at least some cancer cells that carry a mutation in the human PIK3CA gene or carry more than two alleles of this gene. The human PIK3CA gene encodes the p110α protein, which is a catalytic subunit of class I phosphatidylinositol 3-kinases (PI3-kinases). See, e.g., Baselga, 2011, The Oncologist, 16(Suppl. 1):12-19, and references therein.

Molecular biological and other methods for detecting such mutations and genetic amplifications are commonly known in the art and disclosed, for example, in U.S. Pat. No. 8,026,053, the disclosure of which is incorporated herein by reference. For example, a breast cancer biopsy sample can be obtained and genomic and/or RNA can be extracted therefrom. The genomic DNA can then be analyzed by PCR, DNA sequencing and Southern blotting, for example, to detect point mutations, larger rearrangements or gene amplifications in/of the human PIK3CA gene. Alternatively, the RNA can be reverse transcribed and the resulting cDNA analyzed for such mutations. See, e.g., Sambrook et al., Molecular cloning: a laboratory manual, Cold Spring Harbor Press, 2001. Body fluid biomarkers can also be tested, including circulating tumor cells, nucleic acids (DNA and RNA) originating from tumor cells and circulating in serum or plasma, urine, and saliva.

In other embodiments of the present invention, at least some cancer cells of the breast cancer express a truncated ErbB2 receptor that lacks the extracellular domain to which trastuzumab usually binds. The ErbB2 receptor and its gene have been extensively researched. Molecular biological, immunological and other methods for detecting truncated ErbB2 receptor protein or mutations in the gene that result in a truncated ErbB2 receptor are commonly known in the art.

In other embodiments of the present invention, the breast cancer overexpresses RTKs, for example members of the EGFR family, IGF-1R and HGFR. The EGFR family, IGF-1R and HGFR have been extensively researched. Molecular biological, immunological and other methods for detecting overexpression or amplification of any of these receptors in breast cancer are commonly known in the art.

Throughout this application, various publications are referenced. These publications are hereby incorporated into this application by reference in their entireties to more fully describe the state of the art to which this invention pertains. The following examples further illustrate the invention, but should not be construed to limit the scope of the invention in any way.

EXAMPLES

Example 1

EXEL-7647 Inhibits SRC Kinase Activity

Inhibition of SRC kinase activity by EXEL-7647 was measured using in vitro kinase assays. These experiments showed that EXEL-7647 inhibited SCR kinase activity with an $IC_{50}$ of 10.3 nM±2.0 (data not shown). In addition, the effect of EXEL-7647 on the phosphorylation of the SRC-family protein FAK (focal adhesion kinase) was measured in cell culture (FIG. 1). Specifically, DLD1-PTK2 cells were treated with EXEL-7647 at concentrations of 1.6, 4.7, 14, 41, 123, 370, 1111, 3333 or 10,000 nM for one hour in serum-free DMEM and harvested. The phosphorylation status of the tyrosine at amino acid position 861 of the FAK protein ("FAK-PY861") in the treated cells was then determined by standard Western blotting using phosphorylation-specific antibodies, as indicated in FIG. 1. The Western blot was quantified using a Typhoon scanned image and ImageQuant software and the $IC_{50}$ value for EXEL-7647-mediated inhibition of FAK-phosphorylation calculated. EXEL-7647 inhibited phosphorylation of FAK at the tyrosine at amino acid position 861 with an $IC_{50}$ of about 1 μM. The kinase inhibitor staurosporine (EXEL 00878128) was used as a positive control. The inhibition of FAK-autophosphorylation of the tyrosine at amino acid position 397 ("FAK-PY397") was also assayed, as indicated in FIG. 1, but not further quantified. The identifier EXEL-02377647:9 in FIG. 1 refers to compound EXEL-7647.

Example 2

EXEL-7647 Inhibits Growth of Breast Cancer Xenografts

The human breast cancer cell line BT474 expresses high levels of ErbB2 (Her2), a significant fraction of which is constitutively phosphorylated even in the absence of an exogenous ligand. The phosphorylation of ErbB2 is a measure of its activity. Athymic nude mice bearing tumor xenografts derived from the human breast cancer cell line BT474 were treated orally on three consecutive days with 3, 10, 30 or 100 mg/kg of EXEL-7647. The tumors were harvested 1 hr after the final dose was administered and their weights were measured. The calculated $ED_{50}$ of EXEL-7647-mediated inhibition of tumor growth was 30 mg EXEL-7647 per kg of body weight (data not shown).

Example 3

EXEL-7647 Inhibits ErbB2 (Her2) Phosphorylation

Figure 2:
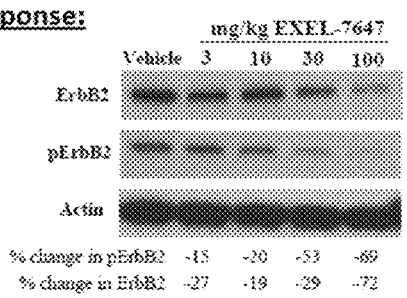
FIG. 2 shows the effect of EXEL-7647 on ErbB2 (Her2)-phosphorylation in BT474 tumor xenografts in mice.
Figure 2:
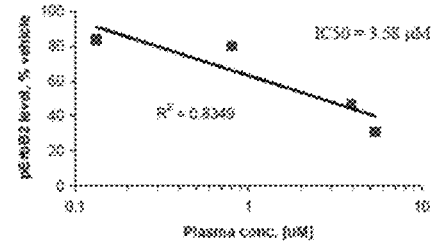
Figure 2:
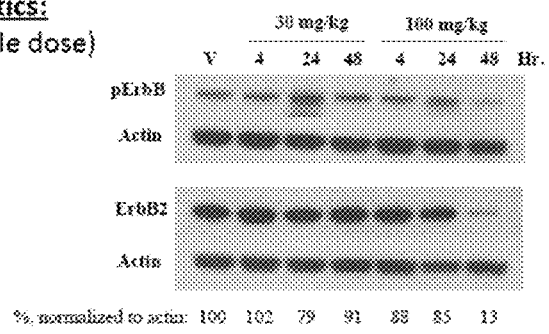
Figure 2:
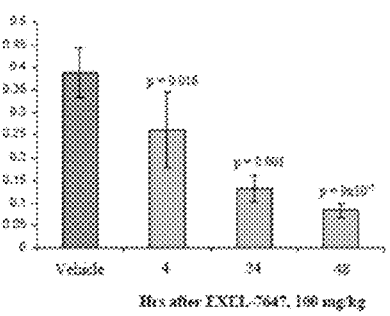

Tumors generated as described in Example 2 above were assayed individually or in treatment groups for total and phospho-ErbB2 levels by standard Western blotting (FIG. 2, top left panel). Tumors from mice treated with vehicle alone served as the negative control. The detection of actin served as a control for protein integrity and concentration. It is readily apparent that XL647 induced a dose-dependent decrease in total and phospho-ErbB2 levels. Decreases were calculated by reference to the vehicle control. For example, a dose of 100 mg/kg of EXEL-7647, administered on three consecutive days, resulted in a reduction of phospho-ErbB2 of approximately 70%.

The plasma concentrations of EXEL-7647 in the mice carrying the analyzed tumors (see above) were determined as well and correlated with the corresponding phospho-ErbB2 levels (FIG. 2, top right panel). These measurements revealed that EXEL-7647 inhibited the accumulation of phospho-ErbB2 in the tumors with an $IC_{50}$ of 3.58 µM, and that a plasma concentration of EXEL-7647 of about 5.37 µM resulted in an approximately 69% reduction of phospho-ErbB2.

The kinetics of the decrease of phospho-ErbB2 in tumors in response to single doses of EXEL-7647 was also determined (FIG. 2, bottom left panel). Tumors were generated as described above. Tumor bearing mice were subjected to a single dose of EXEL-7647 (30 or 100 mg/kg), and tumors were dissected and lysates prepared 4, 24 or 48 hours after dosing. Total and phospho-ErbB2 content in the lysates was determined and decreases in ErbB2 levels calculated as described above. Overall, total and phospho-ErbB2 amounts were not significantly reduced in response to a dose of 30 mg/kg of EXEL-7647. In response to a dose of 100 mg/kg, however, there was a significant reduction, especially after 24 and 48 hours. The histogram in FIG. 2, bottom right panel, shows the kinetics of phospho-ErbB2 decrease in response to a dose of 100 mg/kg of EXEL-7647. As can be seen, the decrease of phospho-ErbB2 is statistically significant ($p<0.05$).

Example 4

EXEL-7647 Inhibits EGFR Phosphorylation

The ability of EXEL-7647 to inhibit the EGF-induced phosphorylation of EGFR was validated as follows. Athymic nude mice bearing tumor xenografts derived from the human epithelial carcinoma cell line A431 were treated orally with 3, 10, 30 or 100 mg/kg EXEL-7647. Three and half hours after EXEL-7647 treatment, EGF was administered intravenously to induce EGF-phosphorylation. The tumors were then harvested and their phospho-EGFR (pEGFR) content was measured. Tumors from mice treated with vehicle alone served as the negative control and tumors from mice treated with vehicle and EGFR served as the positive control. The histogram in FIG. 3, left panel, shows the decrease of EGF-induced EGFR-phosphorylation in the tumors in response to the different doses of EXEL-7647 administered. For example, a dose of 100 mg/kg EXEL-7647 resulted in a reduction of EGF-induced EGFR-phosphorylation of about 90% by comparison to the positive control. As can be seen, the reduction of EGF-induced EGFR-phosphorylation in response to the different EXEL-7647 doses administered is statistically significant ($p<0.05$).

Figure 3:
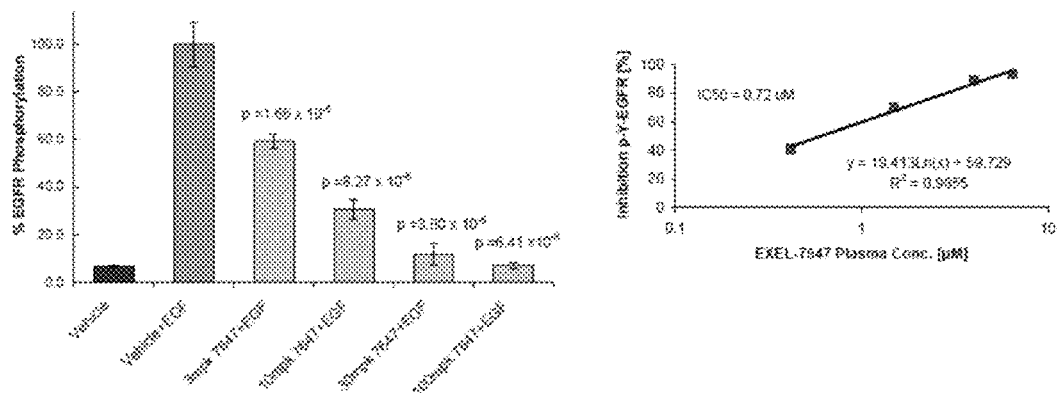
FIG. 3 shows the effect of EXEL-7647 on EGFR-phosphorylation in A431 tumor xenografts in mice.

The plasma concentrations of EXEL-7647 in the mice carrying the analyzed tumors (see above) were determined as well and correlated with the corresponding reduction of phospho-EGFR levels (FIG. 3, right panel). These measurements revealed that EXEL-7647 inhibited the phosphorylation of EGFR in the tumors with an $IC_{50}$ plasma concentration of 0.72 µM.

Example 5

EXEL-7647 Inhibits KDR Phosphorylation

Figure 4:
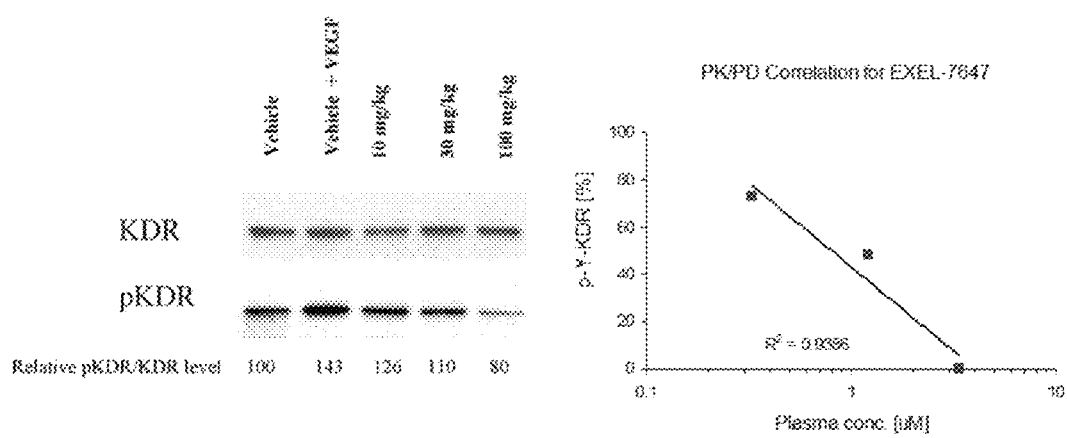
FIG. 4 shows the effect of EXEL-7647 on KDR-phosphorylation in mouse lungs.

Highly vascularized tissue such as the lung of mice contains significant levels of KDR, but only a small fraction of it is in the phosphorylated form. Intravenous administration to mice of 10 µg of VEGF, the ligand of KDR, increased the amount of phospho-KDR (pKDR) in their lungs about 1.5 fold after 30 minutes. The ability of EXEL-7647 to inhibit the VEGF-induced activation of the KDR receptor (determined by measuring the receptor's level of phosphorylation) was validated as follows. Mice were treated orally with a single dose of 10, 30 or 100 mg/kg of EXEL-7647. Three and half hours after EXEL-7647 treatment, 10 µg of VEGF were administered intravenously. The lungs were then harvested and lysates from each dosage group (n=5) pooled. Lysates were assayed for total KDR and pKDR levels by standard Western blotting (FIG. 4, left panel). Lungs from mice treated with vehicle alone served as the negative control and lungs from mice treated with vehicle and VEGF served as the positive control. It is readily apparent that administration of EXEL-7647 resulted in a dose-dependent decrease of VEGF-induced KDR-phosphorylation. Decreases were calculated by reference to the vehicle control. For example, a single dose of 100 mg/kg EXEL-7647 completely suppressed VEGF-induced KDR receptor phosphorylation to baseline levels. Quantification of p-KDR in lysates from individual mice confirmed both the statistical significance of VEGF-induced KDR-phosphorylation ($p<0.0005$) and the statistical significance of the complete inhibition of this induction by the administration of 100 mg/kg of EXEL-7647 ($p<0.001$) (data not shown).

The plasma concentrations of EXEL-7647 in the treated mice (see above) were determined as well and correlated with the corresponding decrease of VEGF-induced KDR-phosphorylation measured in lysate pools (FIG. 4, right panel). These measurements revealed that EXEL-7647 decreased the VEGF-induced KDR receptor phosphorylation with an $IC_{50}$ of about 1.23 µM, and that a plasma concentration of about 3.36 µM of EXEL-7647 resulted in the complete inhibition of KDR-phosphorylation in response to VEGF treatment.

Example 6

EXEL-7647 Inhibits EphB4 Phosphorylation

The ability of EXEL-7647 to inhibit the activity of the EphB4 receptor (determined by measuring the receptor's level of phosphorylation) was validated as follows. A cell line expressing high levels of EphB4 was derived by transfecting the human colon carcinoma line HCT116 with a drug selectable marker and an expression vector encoding EphB4. The resulting EphB4 expressing cells (HCT116/EphB4) grow as xenografts in immunocompromised mice. Analysis of lysates from these xenografts showed that a significant amount of EphB4 in the cells is constitutively phosphorylated at a tyrosine residue. Attempts to further stimulate EphB4-phosphorylation by intravenous or intratumoral injection of Eph A2 were not successful (data not shown).

Figure 5:
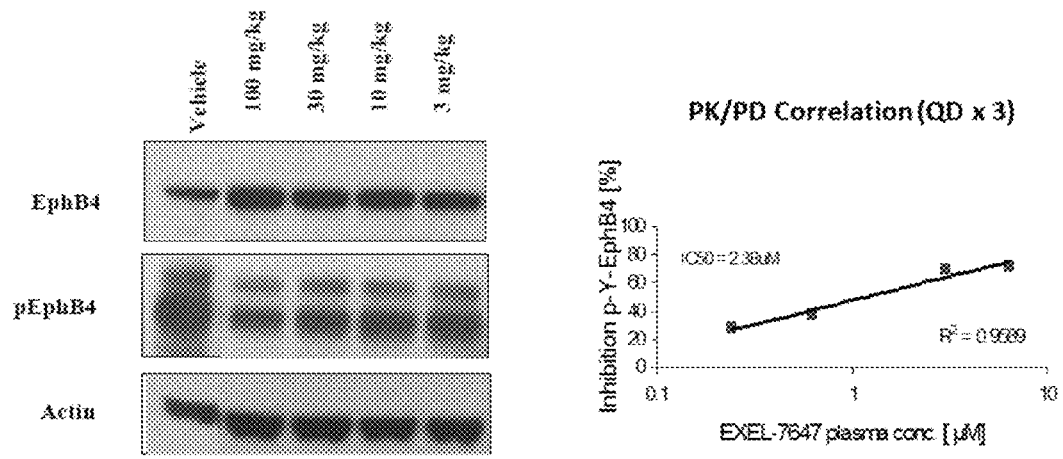
FIG. 5 shows the effect of EXEL-7647 on EphB4-phosphorylation in HCT116/EphB4 xenografts in mice.

Mice bearing HCT116/EphB4 xenografts were dosed orally on three consecutive days with 3, 10, 30 or 100 mg/kg EXEL-7647. Tumors were harvested 1 hr after the final dose and assayed individually or in treatment groups for total and phospho-EphB4 levels by standard Western blotting (FIG. 5, left panel). Tumors from mice treated with vehicle alone served as the negative control. The detection of actin served as a control for protein integrity and concentration. EXEL-7647 induced a dose-dependent decrease in phospho-EphB4 levels. Specifically, a dose of 100 mg/kg of EXEL-7647, administered on three consecutive days, resulted in a reduction of phospho-EphB4 of approximately 70%.

The plasma concentrations of EXEL-7647 in the mice carrying the analyzed tumors (see above) were determined as well and correlated with the corresponding reductions of phospho-EPHB4 levels (FIG. 5, right panel). These measurements revealed that a EXEL-7647 plasma concentration of about 3 µM reduced the phosphorylation of EphB4 in the tumors by approximately 70%. A 50% inhibition of EphB4-phosphorylation was predicted to occur at a EXEL-7647 plasma concentration of about 2.4 µM.

Example 7

EXEL-7647 Inhibits Angiogenesis

Figure 6:
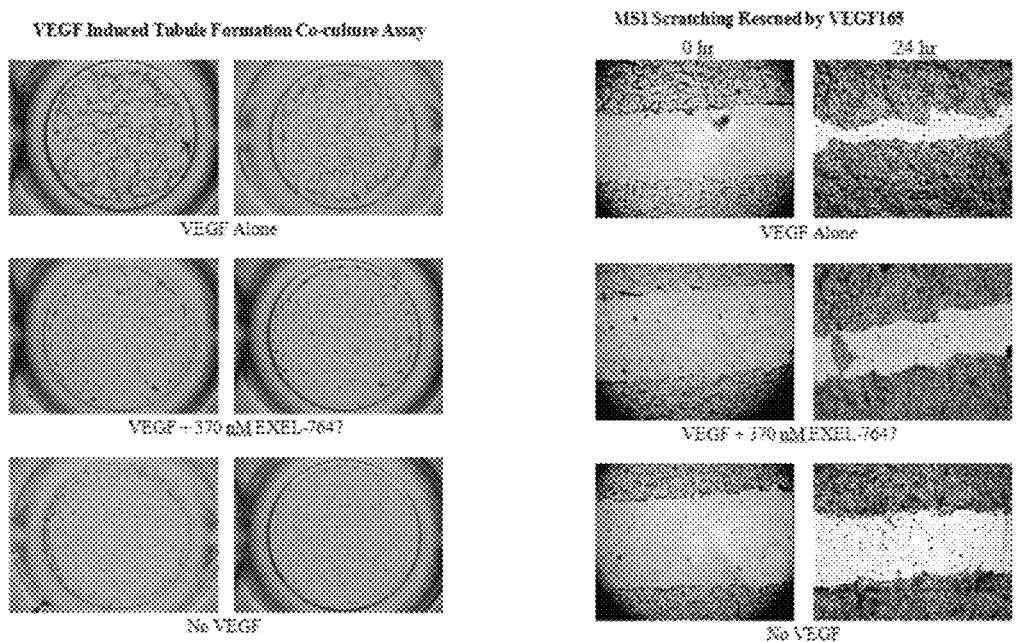
FIG. 6 shows the effect of EXEL-7647 on angiogenesis.

The ability of EXEL-7647 to inhibit angiogenesis was validated by in vitro and in vivo experiments, as shown below (FIG. 6; Table 2). Endothelial tube formation and cell migration assays were performed to test the effect of EXEL-7647 on in vitro models that reflect aspects of endothelial cell function thought to contribute to angiogenesis in vivo. When plated on a confluent layer of normal human diploid fibroblasts, human microvascular endothelial cells (HMVECs) form extensive networks of tubules in response to VEGF over a 7-10 day period. Tubules were stained and quantified using an antibody that recognizes the endothelial cell marker CD31, as illustrated in FIG. 6, left panel. EXEL-7647 inhibited VEGF-induced tubule formation with an $IC_{50}$ of approximately 0.22 µM, which was similar to the $IC_{50}$ values obtained using the receptor phosphorylation assays discussed above in Examples 3-6. The $IC_{50}$ for cytotoxic effects of EXEL-7647 on HMVECs, as determined by Alamar blue staining, was about 1.3 µM, approximately 5-fold higher than the $IC_{50}$ with which EXEL-7647 inhibits VEGF-induced tubule formation (data not shown).

A second assay, the so-called "scratch assay," was employed to examine the effects of EXEL-7647 on murine endothelial cells (FIG. 6, right panel). In this assay, a cell-free zone was scratched into a monolayer of cells and the ability of EXEL-7647 to block VEGF-stimulated migration of murine MS1 endothelial cells into the cell-free zone was measured. In the absence of VEGF, migration of cells bordering the scratch into the cell-free space was minimal during the 24 hrs time-course of the experiment. VEGF greatly stimulated migration, resulting in a nearly complete closure of the scratch within that time frame. EXEL-7647 inhibited cellular migration into the scratch with an $IC_{50}$ of about 0.12 µM, as determined from a six-point dose response. (FIG. 6, right panel). This is consistent with EXEL-7647 inhibiting the murine KDR receptor and the human KDR receptor to a similar extent. No evidence for cytotoxicity of EXEL-7647 was found in this assay at concentrations below 1.1 µM.

Anti-angiogenic effects of EXEL-7647 were also studied in vivo. Tumor xenografts derived from the human breast cancer cell line MDA-MB-231 were established in athymic female mice and allowed to reach a total weight of 100 mg. The mice were then treated orally on fourteen consecutive days with doses of 10, 30 or 100 mg/kg of EXEL-7647. The tumors were harvested and their weights were measured after the last dosage had been administered. Tumors derived from mice treated with vehicle alone served as negative controls. Tumor growth was inhibited significantly by all three dosage regimens (data not shown). Specifically, the 100 mg/kg dosage resulted in a complete cessation of tumor growth (tumor weight at start of study=100.6±8.7 mg, tumor weight at end of study 112±16.2 mg). The 30 and 100 mg/kg regimens also significantly increased the percentage of total tumor necrosis when compared to the necrosis in control tumors treated with vehicle alone (Table 2 below). A statistically significant increase in tumor necrosis was not observed at the lower dose of 10 mg/kg in this model. Furthermore, the amount of CD31-positive blood vessels was significantly decreased in the viable tissue of those tumors that were derived from mice subjected to any of the three dosage regimens tested (Table 2 below). Finally, the percentage of cells expressing Ki67, a marker for cell proliferation, was significantly reduced in the tumors that were derived from mice subjected to any of the three dosage regimens tested (Table 2). This indicated that these tumors contained fewer proliferating cells.

TABLE 2

Anti-Angiogenesis and Other Effects of XL647 in vivo

| KD-019 Dose | Necrosis % increase | Necrosis fold increase | CD31 Analysis MVC* | CD31 Analysis % Reduction | Ki67 Expression % of Cells | Ki67 Expression % Reduction |
|---|---|---|---|---|---|---|
| Vehicle | 15.7 (7.3) | N.A. | 18.5 (6.4) | N.A | 49.4 (10.2) | N.A. |
| 10 mg/kg | 25.0 (14.2) | 1.6 | 12.93 (2.3) | 30.23 | 29.8 (13.3) | 39.6 |

TABLE 2-continued

Anti-Angiogenesis and Other Effects of XL647 in vivo

| KD-019 Dose | Necrosis % increase | Necrosis fold increase | CD31 Analysis MVC* | CD31 Analysis % Reduction | Ki67 Expression % of Cells | Ki67 Expression % Reduction |
|---|---|---|---|---|---|---|
| 30 mg/kg | 30.6 (11.3) | 2.0 | 8.18 (1.4) | 55.83 | 28.3 (10.4) | 42.6 |
| 100 mg/kg | 71.1 (8.1) | 4.5 | 1.625 (1) | 91.23 | 24.87 (4.9) | 49.6 |

*MVC stands for mean vessel count.
**Values are means with the standard deviations being in parentheses.

Example 8

EXEL-7647 Inhibits Growth of Breast Cancer Xenografts

Figure 7:
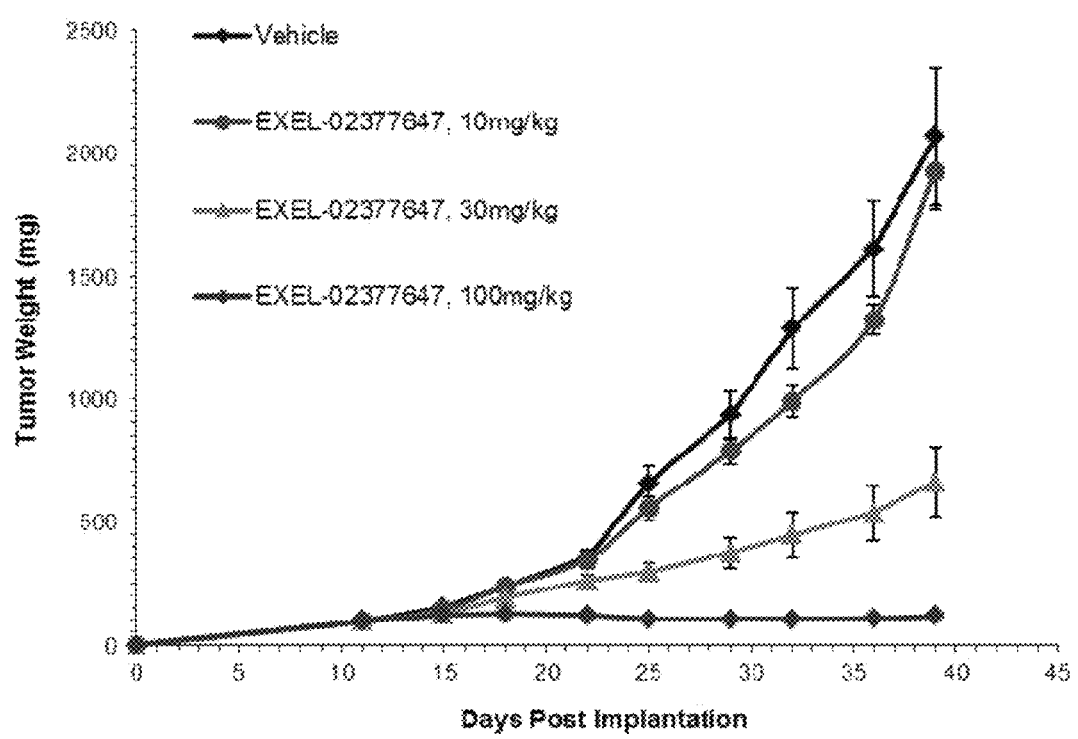
FIG. 7 shows the effect of EXEL-7647 on the growth of MDA-MB-231 tumor xenografts in mice.

The ability of EXEL-7647 to inhibit the growth of tumors derived from the human breast cancer cell line MDA-MB-231 was validated as follows. Tumor xenografts derived from MDA-MB-231 cells were established in athymic female mice and allowed to reach a total weight of 100 mg. The mice were then treated orally on up to twenty-eight consecutive days with doses of 10, 30 or 100 mg/kg of EXEL-7647. The tumors were harvested on specific days after treatment with XL647 had begun and their weights were measured, as indicated in FIG. 7. Tumors derived from mice treated with vehicle alone served as negative controls. Tumor growth was inhibited significantly by the administration of the 30 and the 100 mg/kg of EXEL-7647 dosages (FIG. 7). Specifically, the 100 mg/kg dosage resulted in a complete arrest of tumor growth (starting tumor weight 94±9 mg, final tumor weight 117±33 mg). The calculated $ED_{50}$ of EXEL-7647-mediated inhibition of tumor growth was 22.9 mg of XL647 per kg body weight.

Example 9

EXEL-7647 Supresses Trastuzumab Resistant Cell Proliferation

A significant proportion of ERBB2 positive breast cancer patients does not respond or becomes resistant to trastuzumab treatment. Resistance arises largely via genetic alteration in RTKs and other signaling molecules downstream of the receptors or via upregulation of the activity of other RTKs as a compensatory mechanism. EXEL-7647 is potently active in models of trastuzumab resistance, as demonstrated by growth inhibition of JIMT-1 and HCC1954 trastuzumab resistant cancer cell lines.

JIMT-1 and HCC1954 cells were seeded into 96-well plates (Costar), in Dulbecco's Modification of Eagle's Medium (DMEM, Invitrogen) containing 10% Fetal Bovine Serum (heat inactivated FBS, Hyclone), 1% Penicillin-streptomycin (Hyclone). 18 hours after seeding, cells were treated with the compounds for 72 hours. Triplicate wells were used for each compound concentration. The control wells were treated with 0.2% DMSO media. The cultures were incubated at 37° C., 5% CO2 and the quantity of proliferating cells was determined using the "CellTiter 96 AQueous Non-Radioactive Cell Proliferation Assay kit" (Promega). Following incubation with the substrate solution, the plate was read using Infinite M1000 plate reader (Tecan). $IC_{50}$ values were calculated based on the GraphPad Prism software analysis. Percentage inhibition of cell proliferation was calculated as [1−(treated cells/control cells)× 100].

Treatment of either cell line with increasing concentrations of trastuzumab had no impact of the rate of cellular proliferation, confirming that JIMT-1 and HCC1954 cell lines are not responsive to trastuzumab treatment. However, EXEL-7647 strongly inhibited proliferation of these cells (Table 3 and 4).

TABLE 3

Inhibition of JIMT-1 cell proliferation (% inhibition)

| EXEL-7647 | DMSO | Trastuzumab | | | | |
|---|---|---|---|---|---|---|
| | | 0.2 µg/ml | 0.5 µg/ml | 1.0 µg/ml | 2.0 µg/ml | 5.0 µg/ml |
| DMSO | 0 | 1.9 | 3.4 | 4.4 | −1.8 | −6.0 |
| 0.2 µM | 15.7 | 7.9 | 7.6 | 11.0 | 11.1 | |
| 0.5 µM | 20.3 | 4.6 | 4.7 | 12.0 | 14.0 | |
| 1.0 µM | 22.7 | 11.8 | 14.3 | 17.4 | 18.9 | |
| 2.0 µM | 28.8 | 28.1 | 27.1 | 27.5 | 27.6 | |
| 5.0 µM | 81.7 | | | | | |

TABLE 4

Inhibition of HCC1954 cell proliferation (% inhibition)

| EXEL-7647 | DMSO | Trastuzumab | | | | |
|---|---|---|---|---|---|---|
| | | 0.2 µg/ml | 0.5 µg/ml | 1.0 µg/ml | 2.0 µg/ml | 5.0 µg/ml |
| DMSO | 0 | −6.9 | −6.4 | −6.5 | −15.5 | −13.9 |
| 0.2 µM | 22.5 | 10.9 | 12.9 | 17.8 | 23.5 | |
| 0.5 µM | 32.6 | 14.3 | 14.4 | 20.3 | 30.4 | |
| 1.0 µM | 38.1 | 25.0 | 27.1 | 29.1 | 39.1 | |
| 2.0 µM | 43.6 | 42.6 | 44.3 | 44.9 | 46.7 | |
| 5.0 µM | 80.4 | | | | | |

To compare the two cell lines directly, total protein levels of SRC family kinases as well as the levels of activating phosphorylation of these proteins were analyzed in both cells lines. Cells were washed twice with ice cold PBS and lysed in RIPA buffer (50 mM Tris at pH 8.0, 150 mM NaCl, 1.0% IGEPAL CA-630, 0.5% sodium deoxycholate, 0.1% SDS, containing protease and phosphatase inhibitor cocktail). Cell lysate was collected after centrifugation (12,000 rpm, 15 minutes) and protein concentrations were measured using BCA reagent (Thermo Fisher Scientific). Equal amounts of proteins were separated on SDS-PAGE and transferred onto a PVDF membrane (Millipore). Membranes were blocked with 5% milk in PBS containing 0.1% Tween 20 (PBST) for 1 hour, and then probed with primary antibodies overnight at 4° C. Membranes were washed with PBST and incubated with secondary antibodies for 1 hour at room temperature. After 3× washes in PBST, blots were visualized with enhanced chemiluminescence reagent following the manufacturer's instructions (Thermo Fisher Scientific).

Figure 8:
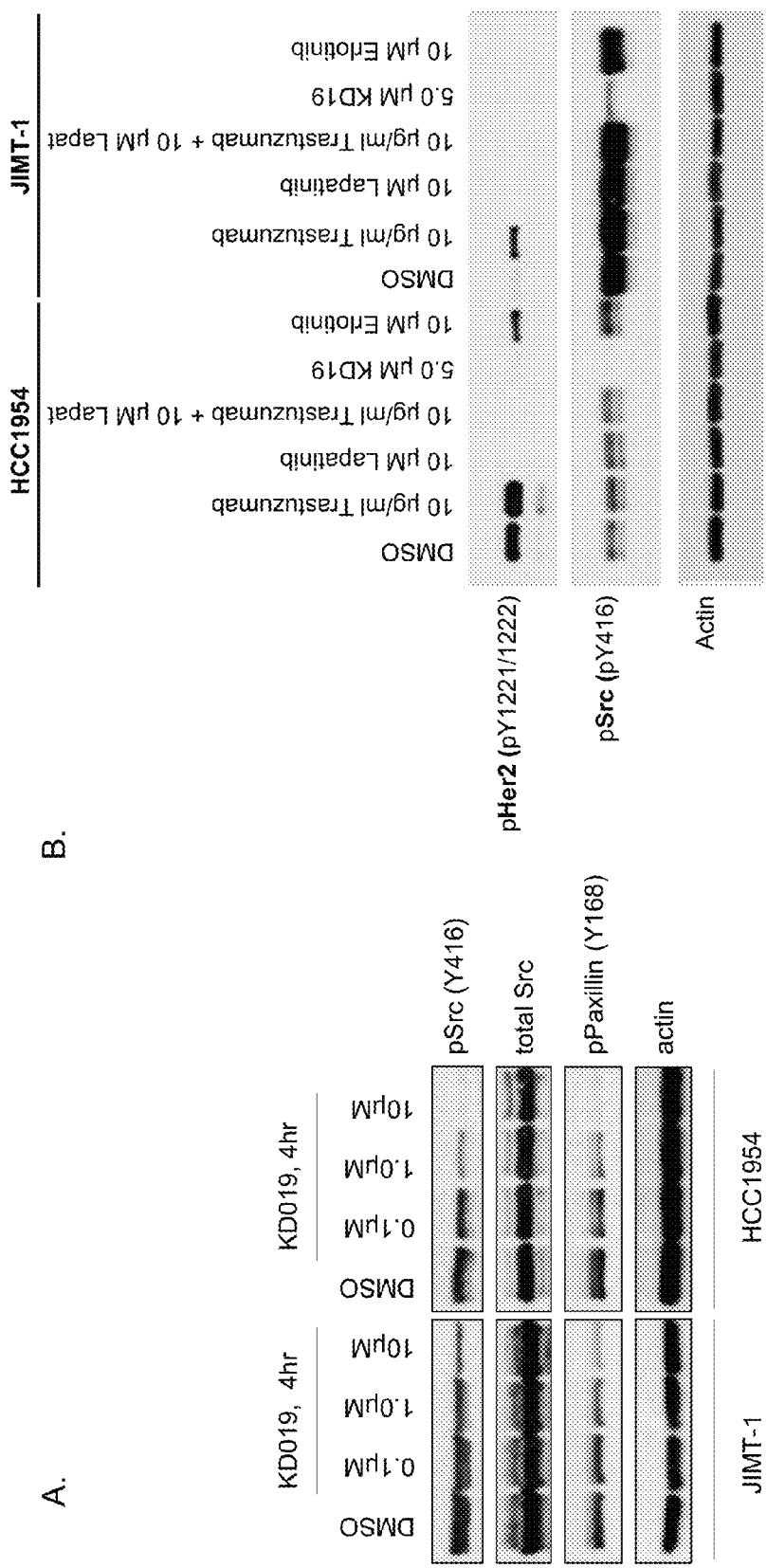
FIG. 8 shows inhibition of Src in traztuzumab resistant cells by EXEL-7647 but not by other ErbB family inhibitors. A) EXEL-7647 inhibits Src in a dose dependent manner B) Phosphorylation of Src in JIMT-1 and HCC1954 cells following treatment with lapatinib, erlotinib, EXEL-7647, and trastuzumab after 18 hours of treatment. C and D) Cell proliferation assay of JIMT-1 (C) and HCC1954 (D) cells treated with EXEL-7647. Cells were treated with the indicated concentrations for 72 hours and cell viability was determined.
Figure 8:
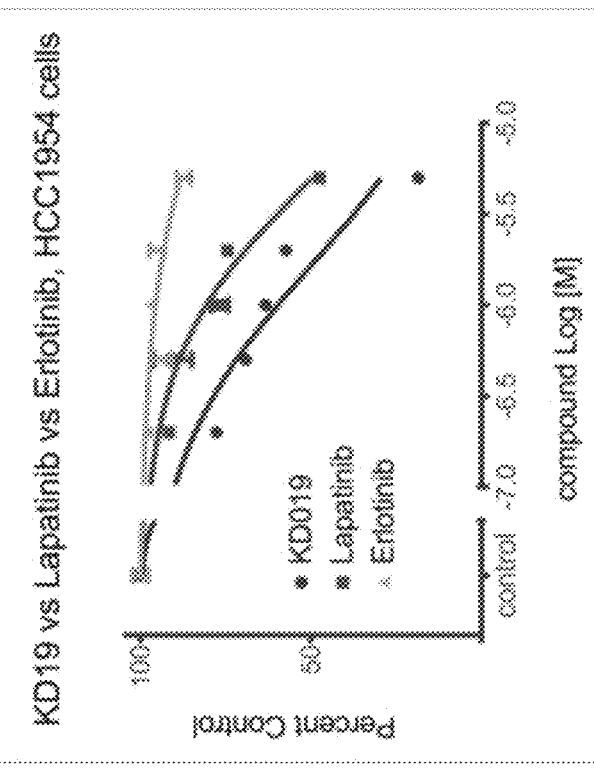
Figure 8:
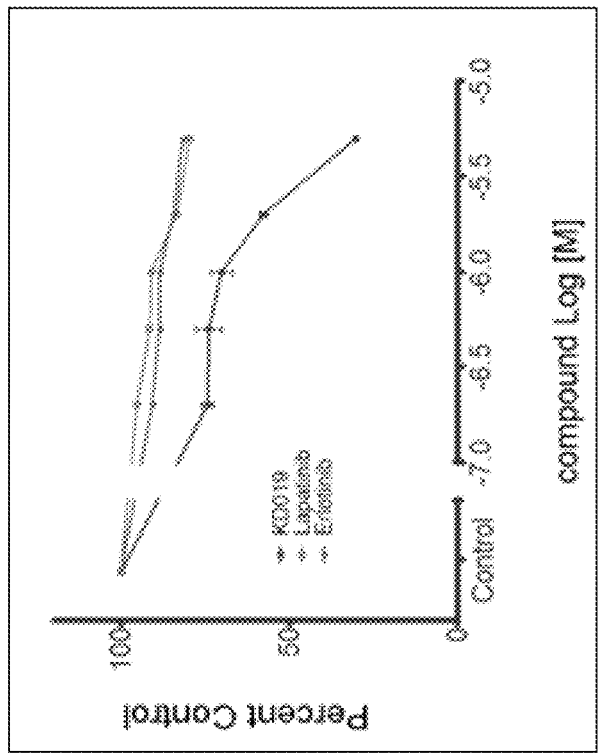

Phosphorylation at tyrosine 416 in the activation loop of the kinase domain of Src correlates with greater activity demonstrated by higher levels of phosphorylation of target proteins including Paxillin. JIMT-1 cells appeared to have significantly greater amounts of SRC proteins than HCC1954 cells (FIG. 8). Consistent with this, treatment with EXEL-7647 had a significantly greater effect on the pSRC levels in HCC1954 cells, where a considerable reduction of phosphor-Src (Tyr416) was achieved by treatment with as low as 0.1 µM EXEL-7647 (FIG. 8A). Importantly, while 4 hr treatment with 1.0 µM EXEL-7647 significantly reduced Src activation, treatment of both cells lines with 5 or 10 µM EXEL-7647 completely abolished phosphorylation of Tyr416, suggesting complete Src inhibition (FIGS. 8A and B). Inhibition of Src activity was further confirmed by the decrease in phosphorylation of Paxillin (Tyr118) (FIG. 8A). To confirm that Src inhibition was direct, SRC phosporylation in EXEL-7647 treated cells was compared to cells treated with other ERBB family inhibitors (FIG. 8B). Only EXEL-7647, and not lapatinib or erlotinib, was able to inhibit SRC activity in both cell lines. In addition, EXEL-7647 had far greater effects on the proliferation of both cell lines in comparison to the other small molecule ERBB inhibitors (FIGS. 8C and D), indicating its ability to treat cells which do not respond to RTK blockade.

Example 10

EXEL-7647 Inhibits Trastuzumab Resistant JIMT-1 Tumor Xenografts

Female severe combined immunodeficient mice (Fox Chase SCID®, C.B-17/Icr-Prkde$^{scid}$, Charles River Laboratories) were ten weeks old, with a body weight range of 17.6 to 20.8 grams on Day 1 of the study. Treatment began on Day 1 in four groups of mice (n=12) with upstaged subcutaneous JIMT-1 tumors (196-405 mm$^3$). Mice were scheduled to receive EXEL-7647 (80 mg/kg p.o. qd×35) with and without trastuzumab (20 mg/kg i.p. biwk×5). The experiment included a vehicle-treated control group and a trastuzumab monotherapy group. During the study, the EXEL-7647 dosing schedule was modified to once daily on Days 1-19, 28, 29, 32-36, and 39-42, due to toxicity. Tumors were measured twice per week until the study was ended on Day 42. Treatment outcome was determined from percent tumor growth inhibition (% TGI), which evaluated the percent differences in median tumor volumes (MTVs) between treated and control mice at the end of daily dosing (Day 18) and at the end of the study (Day 42), with differences between groups deemed statistically significant at P<0.05 using the Mann-Whitney U-test. A regimen that produced TGI of 60% or more was considered to have potential therapeutic activity. Mice were also monitored for complete regression (CR) and partial regression (PR) responses, and for the frequency of 30% tumor volume (TV) regression from Day 1. The 30% TV regressions were deemed statistically significant at P<0.05 using the chi-square test. Treatment tolerability was assessed by body weight measurements and frequent observation for clinical signs of treatment related side effects.

Figure 9:
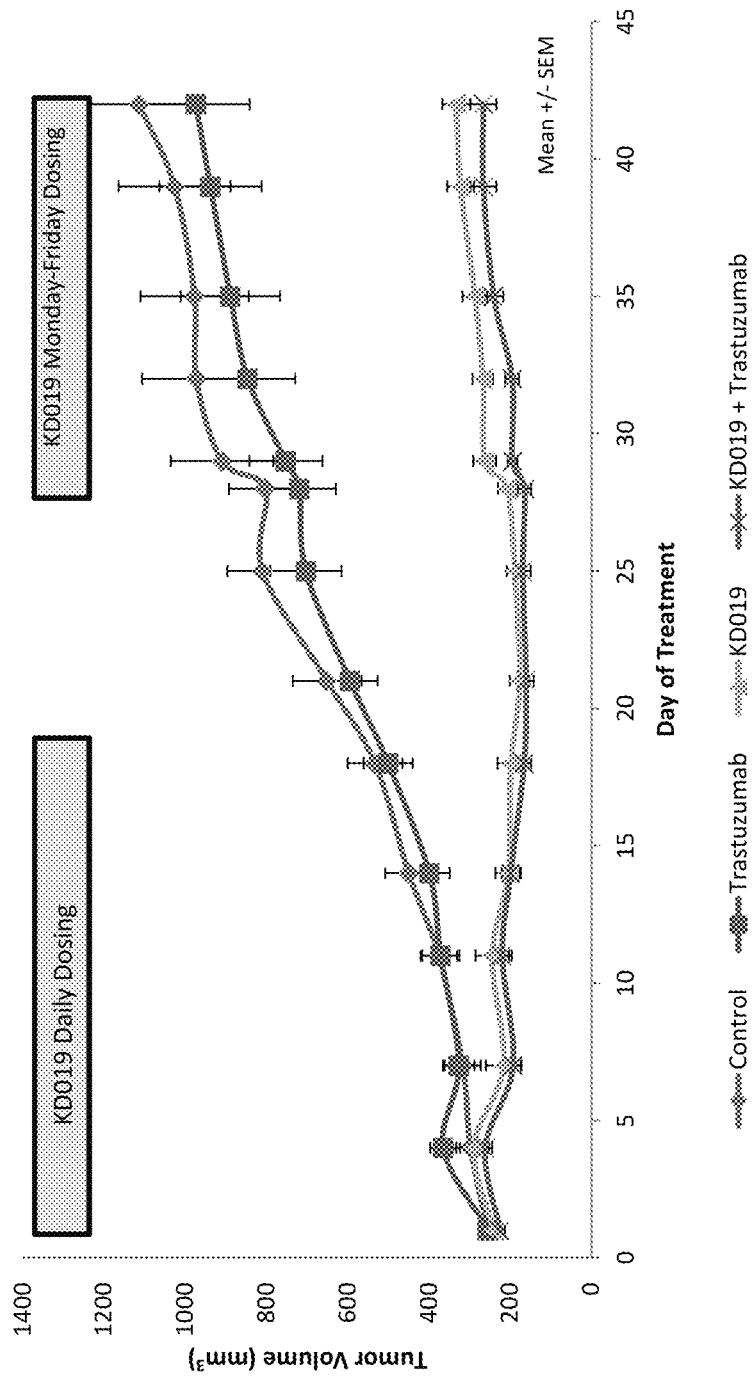
FIG. 9 shows the effect of EXEL-7647, trastuzumab, and a combination of EXEL-7647 and trastuzumab, on growth of trastuzumab resistant JIMT-1 xenograft tumors.

Once established, JIMT-1 tumors are completely resistant to trastuzumab treatment and proliferated at a rate similar to the vehicle control animals. In contrast, 80 mg/kg dose of EXEL-7647 administered orally on a once-daily schedule either alone or in combination with trastuzumab (20 mg/kg i.p. bwk×5) prevented tumor growth (FIG. 9).

Example 11

EXEL-7647 Targets Her2, EGFR and Indirectly Inhibits Met Activation

Figure 10:
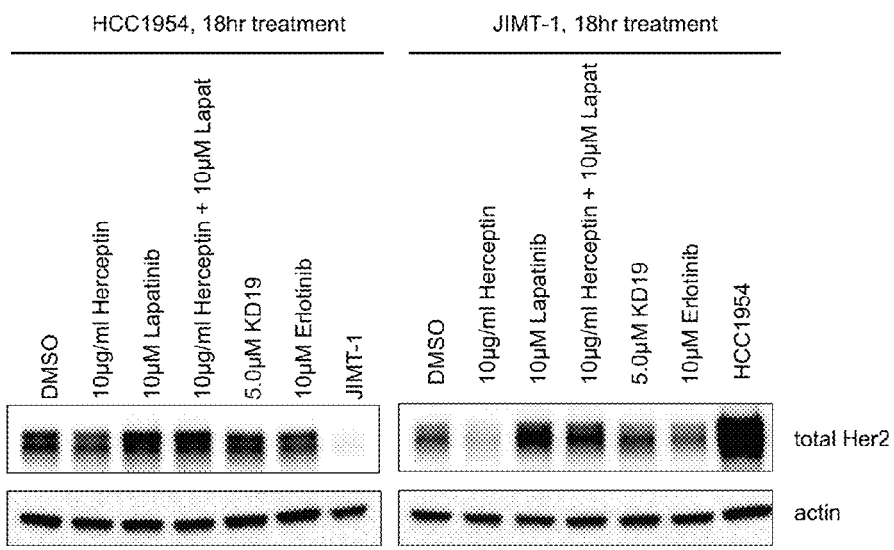
FIG. 10 shows effects of EXEL-7647 on Her2, EGFR, and Met activation. A) JIMT-1 and HCC1954 cells were treated for 18 hours with the indicated compounds. Herceptin, but none of the small molecule inhibitors, affect Her2 expression. B) The small molecule inhibitors, but not herceptin, inhibit Her2 phosphorylation. C) EXEL-7647 inhibits EGFR phosphorylation in HCC1954 and JIMT-1 cells. D) EXEL-7647 inhibits Met phosphorylation in HCC1954 cells.
Figure 10:
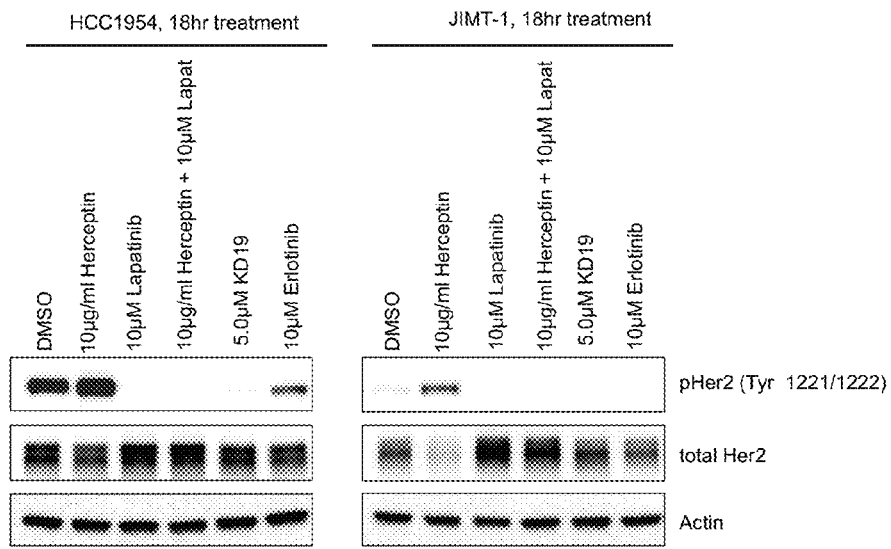
Figure 10:
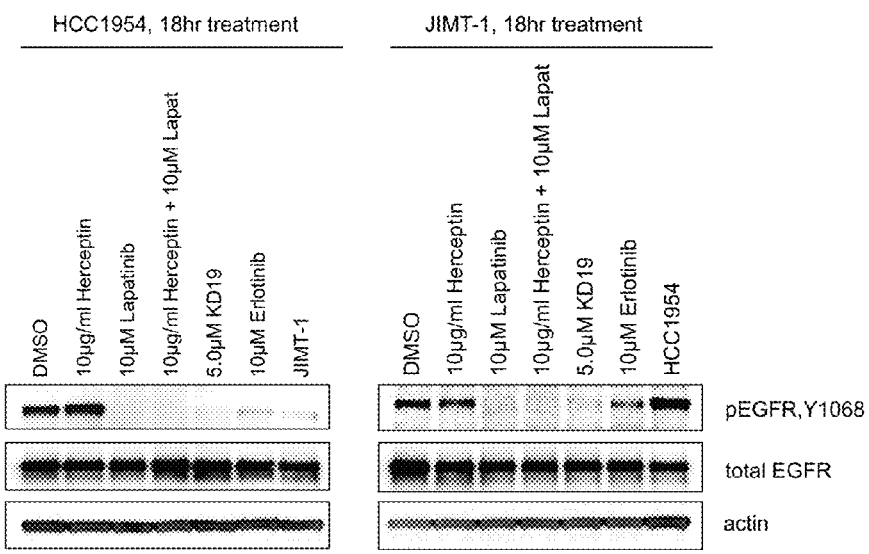
Figure 10:
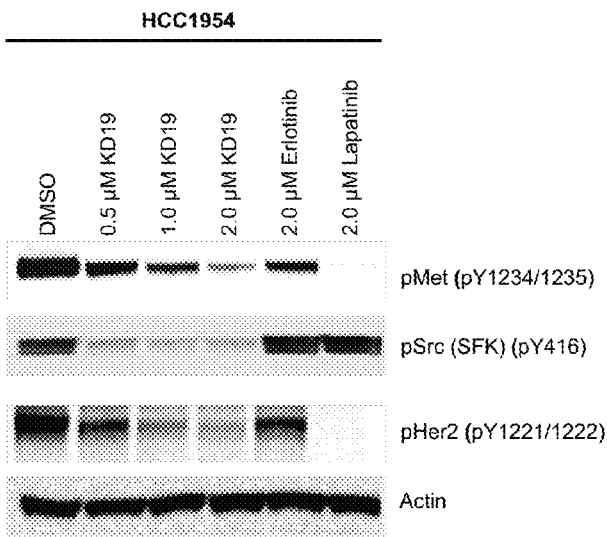

Recent studies indicate that trastuzumab activates phosphorylation of Her2, while simultaneously increasing its internalization and degradation. Consistently, treatment with trastuzumab lead to significant downregulation of total ERBB2 levels in JIMT-1 cells (FIG. 10A, right panel). Like other ERBB family small molecule inhibitors, EXEL-7647 had no effect on the total levels of ERBB2 in these cells, suggesting that receptor turnover does not account for the anti-proliferative qualities of the drug. In HCC1954, no effect on the levels of ERBB2 was observed with any of the treatments, likely due to extremely high expression levels of the receptor in these cells. ERBB2 phosphorylation was elevated in both cell lines following trastuzumab treatment and inhibited by small molecule inhibitors, including EXEL-7647 (FIG. 10B).

Similar results were obtained with the activation of EGFR. While nether trastuzumab nor small molecules changed the overall levels of the receptor in either of the cell lines tested, marked effects were observed on activating EGFR phosphorylation. Here too, HCC1954 expressed the receptor at far greater levels than JIMT-1 cells, and while treatment with trastuzumab had little effect on EGFR phosphorylation, lapatinib, erlotinib and EXEL-7647 inhibited EGFR activity (monitored via phosphorylation of Tyr1068) to a similar extent. Based on the above-mentioned results, we concluded that neither the inhibition of ERBB2 or EGFR activity nor the effects on receptor turnover fully account for the anti-proliferative activity of EXEL-7647.

A high level of active Met phosphorylated at tyrosine sites 1234 and 1235 was also observed in HCC1954 (FIG. 10D) but not in JIMT-1 cells (data not shown). Aberrant activation of Met receptor tyrosine kinase has been linked with trastuzumab resistance. While Met is not a direct target of the molecule, EXEL-7647 effectively inhibited Met activation in HCC1954 cells (FIG. 10D). Inhibition of Met in these cells may be due to receptor hetero-oligomerization, as a similar level of inhibition was observed with lapatinib, which does not have direct Met inhibitory activity.

Example 12

EXEL-7647 Effectively Targets Multiple Kinases

Figure 11:
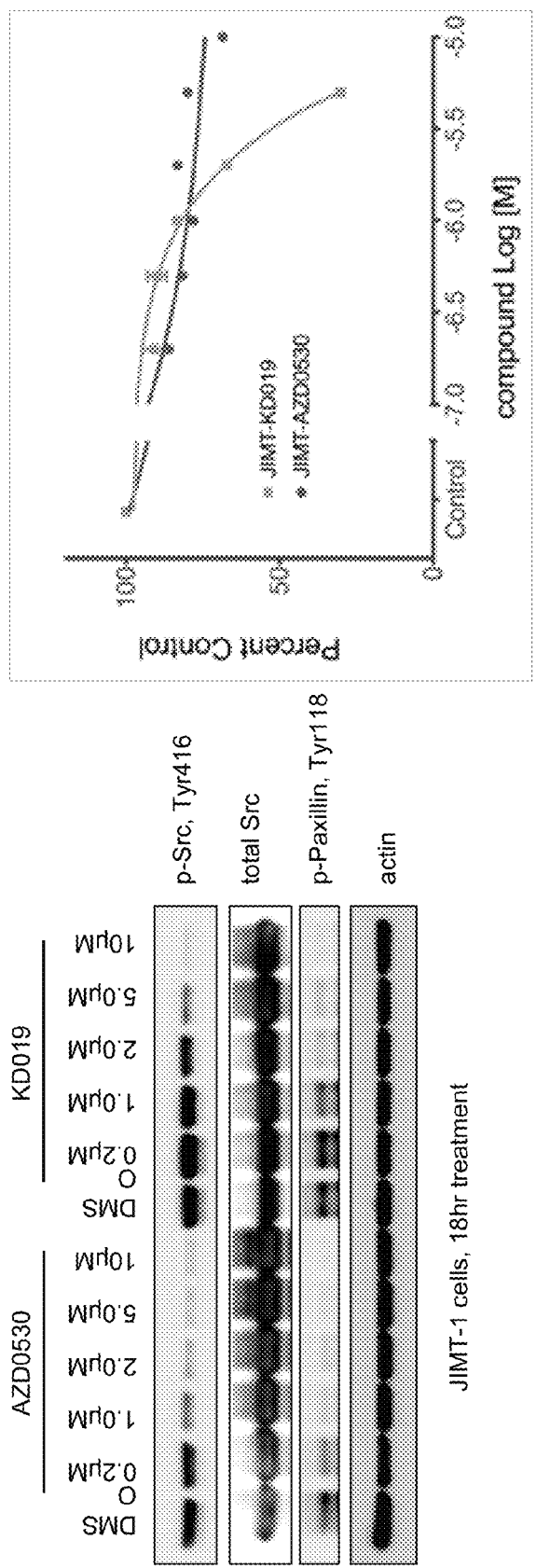
FIG. 11 shows the effect of EXEL-7647 and AZD0530 (saracatinib) on phosphorylation of Src and its target Paxillin phosphorylation, and on proliferation of JIMT-1 cells. A) Phosphorylation of Src and Paxillin in JIMT-1 treated for 18 hrs. with increasing concentrations of KD019 or AZD0530. B) Cell proliferation assay of JIMT-1 cells treated with the indicated concentrations of KD019 or AZD0530. Cell viability was measured by MTS assay after 72 hrs. Error bars represent standard deviation of the average of triplicate wells.

The activity of EXEL-7647 was compared to a selective SRC inhibitor (AZD0530, saracatinib). When compared for their ability to inhibit SRC, AZD0530 exhibited a stronger dose dependent response. In JIMT-1 cells 1.0 µM AZD0530 treatment suppressed Src activity, and although some inhibition was observed at 1.0 µM of EXEL-7647, higher concentrations were required for equivalent inhibition (FIG. 11A). However, in JIMT-1 cells the more potent inhibition of SRC did not directly translate into inhibition of cell growth. In cell proliferation assays, AZD0530 was less effective against JIMT-1 cells than EXEL-7647 (FIG. 11B). The effectiveness of EXEL-7647 is likely a result of its ability to inhibit multiple kinases.

JIMT-1 and HCC1954 cells are two examples of trastuzumab resistance, and represent escape mechanisms for trastuzumab treatment. The experiments presented demonstrate that SRC activation plays an important role development of resistance. EXEL-7647 effectively inhibits proliferation of ERBB2 positive, trastuzumab refractory breast cancer cells.

What is claimed is:

1. A method of treating breast cancer that is nonresponsive to treatment with trastuzumab, comprising administering to a subject in need of such treatment a therapeutically effective amount of a compound of Formula 1

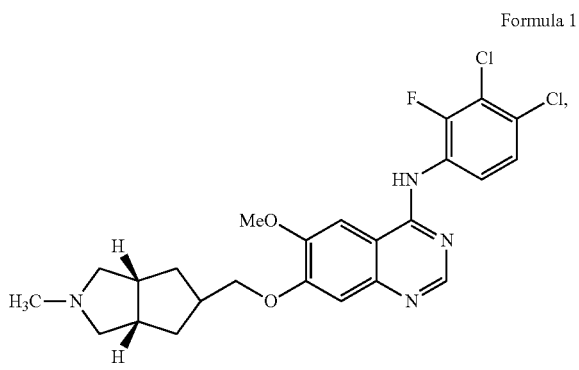 [SMILES: COc1cc2c(Nc3ccc(Cl)c(Cl)c3F)ncnc2cc1OCC1C[C@@H]2CN(C)C[C@@H]2C1]

Formula 1 or a pharmaceutically acceptable salt thereof.

2. The method of claim 1, wherein the compound, or a pharmaceutically acceptable salt thereof, is a stereoisomer selected from the group consisting of N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine and N-(3,4-dichloro-2-fluorophenyl)-7-({[(3 aR, 5 s,6aS)-2-methyloctahydrocyclopenta[c]pyrrol-5-yl]methyl}oxy)-6-(methyloxy)quinazolin-4-amine, or a pharmaceutically acceptable salt of the stereoisomer.

3. The method as in claim 1 or 2, wherein the pharmaceutically acceptable salt is the salt of p-toluenesulfonic acid.

4. The method as in claim 1, 2 or 3, wherein the subject is human and the breast cancer has not been treated with trastuzumab.

5. The method as in claim 1, 2 or 3, wherein the subject is human and the breast cancer has been treated with trastuzumab.

6. The method as in claim 1, 2 or 3, comprising co-administering the compound of Formula 1 and trastuzumab.

7. The method as in claim 1, 2 or 3, wherein the subject is human and the breast cancer is PTEN-negative.

8. The method as in claim 1, 2 or 3, wherein the subject is human and the breast cancer is positive for mutations in the PIK3CA gene.

9. The method as in claim 1, 2 or 3, wherein the subject is human and the breast cancer expresses a truncated ErbB2 receptor that lacks the extracellular domain to which trastuzumab binds.

10. The method as in claim 1, 2 or 3, wherein the subject is human and the breast cancer overexpresses one or more RTKs selected from the group consisting of EGFR family members, IGF-1R and HGFR.

* * * * *